United States Patent [19]
Andoh et al.

[11] Patent Number: 5,624,683
[45] Date of Patent: Apr. 29, 1997

[54] SUSTAINED-RELEASE MULTI-GRANULE TABLET

[75] Inventors: Hidenobu Andoh, Gifu; Sumio Watanabe; Yasuo Miyake, both of Aichi, all of Japan

[73] Assignee: Eisai Co., Ltd., Tokyo, Japan

[21] Appl. No.: 192,603

[22] Filed: Feb. 7, 1994

Related U.S. Application Data

[60] Division of Ser. No. 895,464, Jun. 8, 1992, abandoned, which is a continuation-in-part of Ser. No. 752,987, Sep. 3, 1991, abandoned, which is a continuation of Ser. No. 595,732, Oct. 10, 1990, abandoned, which is a continuation of Ser. No. 240,343, Aug. 25, 1988, abandoned, which is a continuation of Ser. No. 80,012, Jul. 31, 1987, abandoned.

[30] Foreign Application Priority Data

Aug. 6, 1986 [JP] Japan ................................. 61-183414

[51] Int. Cl.⁶ ........................... A61K 9/22; A61K 9/26
[52] U.S. Cl. ................. 424/470; 424/465; 424/468; 424/469; 514/770; 514/774; 514/778; 514/781; 514/782; 514/785; 514/965; 514/960; 514/961
[58] Field of Search ........................... 424/465, 468, 424/470, 490, 493, 494, 469; 514/960, 961, 965

[56] References Cited

U.S. PATENT DOCUMENTS

| | | | |
|---|---|---|---|
| 3,362,880 | 1/1968 | Jeffries | 424/470 |
| 3,388,041 | 6/1968 | Gans | 424/470 |
| 4,017,598 | 4/1977 | Ohno | 424/469 |
| 4,193,985 | 3/1980 | Bechgaard | 424/494 X |
| 4,341,759 | 7/1982 | Bogentoft et al. | 424/21 |
| 4,351,825 | 9/1982 | Sothmann | 424/470 |
| 4,439,453 | 3/1984 | Vogel | 424/470 X |
| 4,572,833 | 2/1986 | Pedersen et al. | 424/20 |
| 4,666,703 | 5/1987 | Kopf | 424/470 |
| 4,716,041 | 12/1987 | Kjornaes | 424/470 |
| 4,748,023 | 5/1988 | Tamas | 424/494 X |

*Primary Examiner*—Thurman K. Page
*Assistant Examiner*—James M. Spear
*Attorney, Agent, or Firm*—Wenderoth, Lind & Ponack

[57] ABSTRACT

A sustained-release multi-granule tablet is obtained by compressing sustained-release granules, which contains a basis, and a formulation adjuvant. Each of the granules has been coated in advance with a layer of the formulation adjuvant and/or a layer of a mixture of the formulation adjuvant and the basis. The tablet releases an active substance at a suitable velocity into the digestion tract, resulting in that the inbalance in the absorption of the drug in each patient and among individual patients is minimized to achieve maximum bioavailability.

24 Claims, 2 Drawing Sheets

SUSTAINED-RELEASE MULTI-GRANULE TABLET

This application is a divisional application of Ser. No. 07/895,464 filed Jun. 8, 1992, now abandoned, which was a continuation-in-part of abandoned application Ser. No. 07/752,987 filed Sep. 3, 1991, which was a continuation of abandoned application Ser. No. 07/595,732 filed Oct. 10, 1990, which was a continuation of abandoned application Ser. No. 07/240,343 filed Aug. 25, 1988, which was a continuation application of abandoned application Ser. No. 080,012 filed Jul. 31, 1987.

BACKGROUND OF THE INVENTION

1. Field of the Invention

This invention relates to a sustained-release multi-granule tablet useful in the field of therapy. More specifically, this invention is concerned with a tablet of the multiple unit type, in which sustained-release granules are contained as a unit.

2. Description of the Prior Art

Sustained-release tablets are a preparation form that is intended to reduce the sufferance of patients by reducing the frequency of administration and at the same time to improve the usefulness of a drug to the maximum in view of both advantageous effects and side effects of the drug.

A certain type of sustained-release tablets take the form of the so-called multiple unit. Namely, a drug is firstly converted into a sustained-release particulate or granular form by a suitable method. A powdery or particulate substance composed of one or more formulation adjuvants is then mixed. The resulting mixture is finally compression-formed or compressed into desired weight, shape and size.

In a drug preparation of the multiple unit type, the drug is divided into a number of granules and is released as an active substance at a suitable velocity into the digestion tract so that the imbalance in the absorption of the drug in each patient and among individual patients is minimized to achieve maximum bioavailability. As typical preparation forms, there are known for example spansule-type capsules in each of which micropills are enclosed in a capsule and tablets of the multiple unit type. The present invention relates to the latter preparation form.

The following two problems have been recognized for many years as drawbacks of tablets of the multiple unit type. The problem of variations in quality is mentioned first of all. In the case of compression-forming, it is generally known that inconsistent mixing occurs due to differences in mixing ratio upon mixing operations, segregation caused by differences in granule number or shape among increments, etc. When tablets of the multiple unit type are produced from sustained-release granules, variations arise as to the contents of the sustained-release granules and the associated granules as a formulation aid by their numbers and their mixing ratio.

Regarding the above-mentioned problem, there is a study conducted by Dr. Shigeo Miwa ["Introduction to Chemical Engineering II", Chapter: "Mixing" (Asakura Shoten)]. From a theoretical curve between the numbers of granules of a drug administered and variation coefficients when the mixing proportion of granules containing an active component is varied in various ways, it is indicated that the variation becomes smaller as the proportion of granules containing the active component increases and the number of granules administered increases.

The present inventors have contemplated how to reduce the variations by applying the above theory to a drug preparation of the multiple unit type. If the proportion of granules containing the active component is increased, the granules are however caused to agglomerate together upon their compression forming and the granules hence become difficult to disperse at the time of the disintegration of the tablet, thereby leading to the loss of the inherent function of the multiple unit. If the number of granules is increased on the other hand, another drawback arises that the preparation form becomes greater.

As the second problem, granules undergo deformation or destruction by high-pressure compression at the time of compression-forming so that the sustained-release function of each unit granule is lost. This may be considered as the largest drawback of multiple unit tablets in a certain sense.

SUMMARY OF THE INVENTION

The present inventors have conducted an extensive research with a view toward developing a process for the formulation of multiple unit tablets which are free from occurrence of agglomeration of granules upon compression forming, are small and have smaller variations in the content of an active component. As a result, it has been found that small tablets of the multiple unit type having smaller variations in the content of an active component can be obtained by coating the surfaces of sustained-release granules as nuclei with layers of a formulation adjuvant and/or layers of a mixture of the formulation adjuvant and an active substance and then compression-forming the thus coated granules.

In one aspect of this invention, it is thus provided a sustained-release multi-granule tablet obtained by compression-forming sustained-release granules, which contains an active substance, and a formulation adjuvant. Each of the granules has been coated in advance with a layer of the formulation adjuvant and/or a layer of a mixture of the formulation adjuvant and the active substance.

By coating the outer surfaces of sustained-release granules with a formulation aid or the like and forming protective coating films thereon, the discreteness of each granule can be enhanced so that their agglomeration upon compression-forming or their deformation or destruction can be avoided.

DETAILED DESCRIPTION OF THE INVENTION AND PREFERRED EMBODIMENTS

Figure 1:
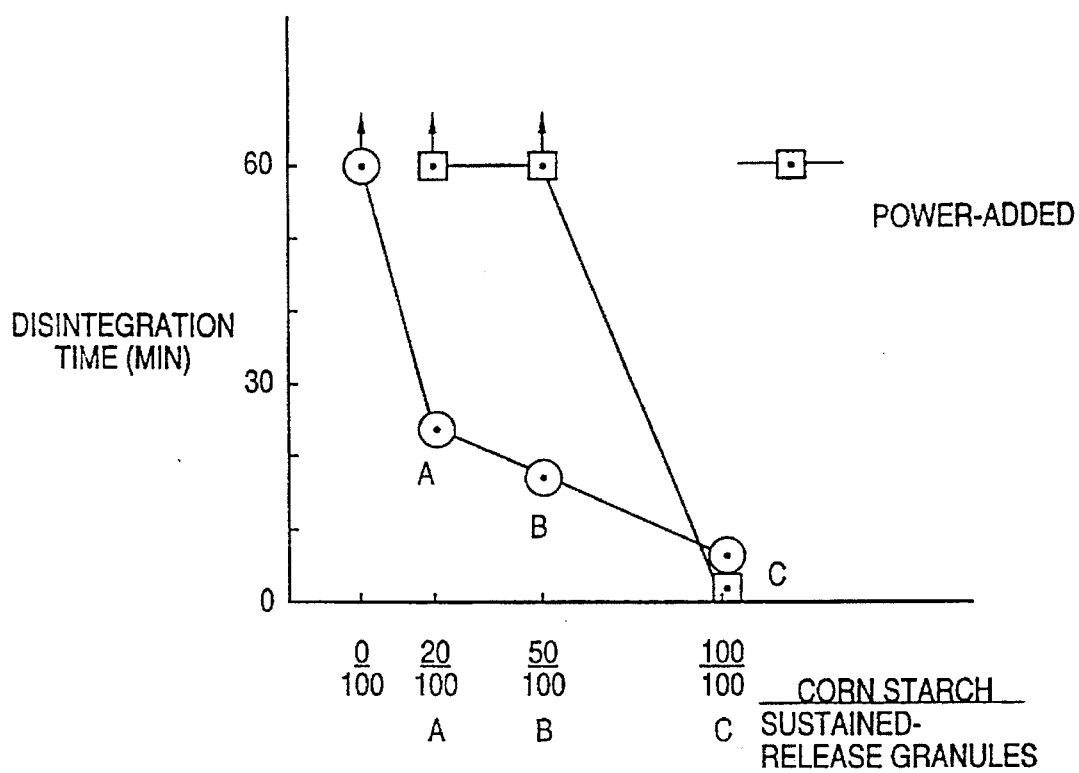
FIG. 1 diagrammatically shows results of disintegration tests of Tablets A, B and C obtained by the coating method in comparison with results of a disintegration test of a tablet obtained by adding powder.

Illustrative examples of the formulation adjuvant in the present invention may include excipients, binders, disintegrators, etc. As exemplary excipients useful in the practice of this invention, may be mentioned Avicel 101, Avicel 301 and Avicel 102 (all trade names, crystalline celluloses), lactose, mannitol, sucrose, corn starch, dextrin, silicic acid, magnesium silicate, aluminum silicate, etc.

As exemplary binders, it is possible to use HPC-L (trade name, hydroxypropylcellulose), PVPK30 and PVPK90 (both trade names, polyvinyl pyrrolidone), PEG6000(trade name, polyethylene glycol), methylcellulose, etc.

As illustrative disintegrators, carboxy methyl, calcium salt of carboxy methyl cellulose (CMC-Ca), sodium crosscarmelose and the like may be used.

The preparation, coating and tablet making operations of sustained-release granules in the present invention can be carried out respectively by conventional procedures such as those mentioned below.

i) Preparation of granules (nuclear granules) to be used as nuclei:

Using a usual cylindrical granulator, nuclear granules are prepared in accordance with the cyclindrical granulating method. That is, a sustained-release granule is prepared using a conventional method from an active substance, i.e. the drug, and a sustained-release substance, e.g. sucrose-fatty acid ester, ethyl cellulose, methyl cellulose, polyvinyl pyrrolidone, hydroxypropyl cellulose, hydroxypropylmethyl cellulose, a gum arabic, gelatin and shellac.

ii) Coating in layers:

The coating is conducted by the rolling granulating method. Namely, nuclear granules and an excipient were mixed in a routine mixer such as super mixer or Henschel mixer. The excipient is preferably a water-soluble or easily water-dispersible substance.

Upon coating, one or more formulation adjuvants such as binders, disintegrators and lubricants may also be added as needed. The lubricant may be a conventional lubricant used in the preparation of pharmaceutical tablets, for example, a running powder and the like such as talc, magnesium stearate and the like.

iii) Tabletting:

Tabletting is conducted using a usual tablet machine. There are the wet tabletting method and dry tabletting method. Tabletting may be effected by either one of these methods. The size of the tablet is preferably in the range of 0.5 to 2.5 mm. The size of the sustained-release nuclear granule is preferably in the range of 0.3 to 2 mm. The ratio of excipient to sustained-release nuclear granule is preferably about 20% by weight or more.

Examples

The constitution and advantageous effects of this invention will hereinafter be described specifically by the following Examples. It should however be borne in mind that the present invention is by no means limited by the following Examples.

Example 1

Sustained-release granules, which had been obtained by granulating in a cylindrical granulating machine equipped with a screen of openings of 0.5 mm across (Model: HV-G; manufactured by Hata Tekkosho K. K.) and then sifting the resultant granules to 16 mesh–60 mesh, were charged in a 1-1 Henschel mixer. While mixing the granules with occasional addition of corn starch and an ethanol solution of PVP K30 in small quantities, the sustained-release granules were coated in layers to give the proportions shown in Table 1.

TABLE 1

(All values indicate weight ratios)

| | Tablet | | |
|---|---|---|---|
| | A | B | C |
| Sustained-release granules | 25 | 25 | 25 |
| Corn starch | 5 | 12.5 | 25 |
| PVP K30 | 0.1 | 0.25 | 0.5 |
| Corn starch/sustained-release granules | 20/100 | 50/100 | 100/100 |

Two hundred milligram portions of the thus-obtained samples were separately weighed precisely and then compression-formed under 400 kg/$\phi$=8 mm by a material testing machine (manufactured by Shimadzu Corp.), whereby tablets were obtained separately.

In the same manner as described above except for the omission of the ethanol solution of PVP K30 as a binder, additional tablets were separately obtained by adding corn starch as is, i.e., in the form of powder or in the form of granules at the same ratio of corn starch to sustained-release granules.

Figure 2:
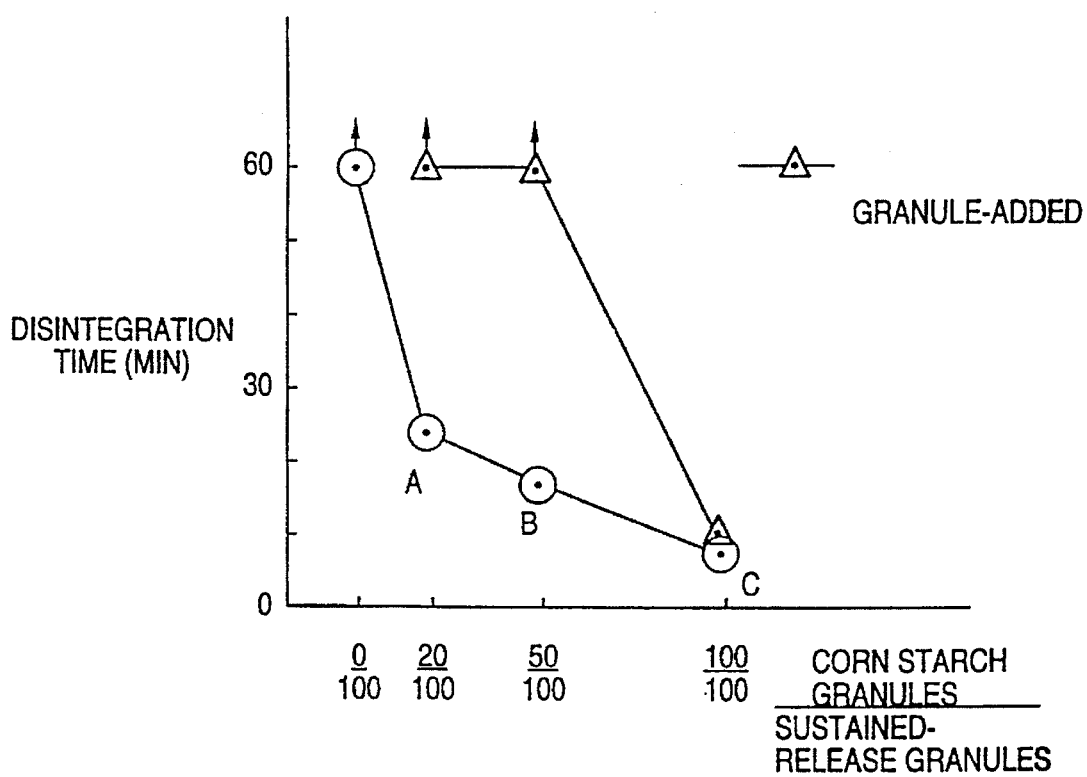
FIG. 2 is also a diagrammatic representation of the results of the disintegration tests of Tablets A, B and C in comparison with results of a disintegration test of a tablet obtained by adding granules.

Disintegration tests were then conducted with respect to the layer-coated tablets (invention products), powder-added tablets and granule-added tablets, all of which had been obtained above. Results are shown diagrammatically in FIGS. 1 and 2.

In each of the drawings, the ratio of corn starch to sustained-release granules is plotted along the axis of abscissas while the disintegration time is plotted in minutes along the axis of ordinates. Plotted points have the following significance:

○. . . Tablets by the layer-coated method (the method of this invention).

☐. . . Powder-added tablets.

△. . . Granule-added tablets.

$\left.\begin{array}{c}\updownarrow \\ \updownarrow \\ \updownarrow\end{array}\right\}$ Indicate plotted values or up.

In addition, coagulation tests were conducted with respect to those tablets. Namely, each tablet was added with 10 ml of water in a weighing bottle. Twenty-four hours later, the disintegration residue was collected by filtration. The coagulated matter (formed by coagulation of two or more granules) in the disintegration residue was then weighed. Results are shown in Table 2.

TABLE 2

(All values are by wt. %)

| Corn starch/sustained-release granules | 20/100 | 50/100 | 100/100 |
|---|---|---|---|
| Layer-coated tablet (this invention) | 0 | 0 | 0 |
| Powder-added tablet | 77.4 | 18.9 | 6.0 |
| Granule-added tablet | 76.3 | 67.4 | 34.2 |

From these results, it is understood that the tablets obtained respectively by the powder-adding method and the granule-adding method are not different in disintegration time from the tablets formed solely of the sustained release granules up to at least a corn starch/sustained-release granule ratio of 50/100 but a significant reduction in disintegration time is observed at a corn starch/sustained-release granule ratio as small as 20/100 in the case of the invention tablets obtained by the layer-coating method. It is also envisaged that the layer-coating method permits the formulation of tablets without coagulation of sustained-release granules.

Example 2

Tablets D, E and F were obtained separately in the same manner as in Example 1 except that portions of corn starch in the respective compositions of Example 1 were replaced by a disintegrator, CMC-Ca, as shown in Table 3. Disintegration and coagulation tests were conducted with respect to those tablets. Results of the disintegration tests will be compared with those of Tablets A, B and C in Example 1.

TABLE 3

(All values indicate weight ratios)

|  | Tablet | | |
|---|---|---|---|
|  | D | E | F |
| Sustained-release granules | 25 | 25 | 25 |
| Corn starch | 4.75 | 11.875 | 23.75 |
| CMC-Ca | 0.25 | 0.625 | 1.25 |
| PVP K30 | 0.1 | 0.25 | 0.5 |

Figure 3:
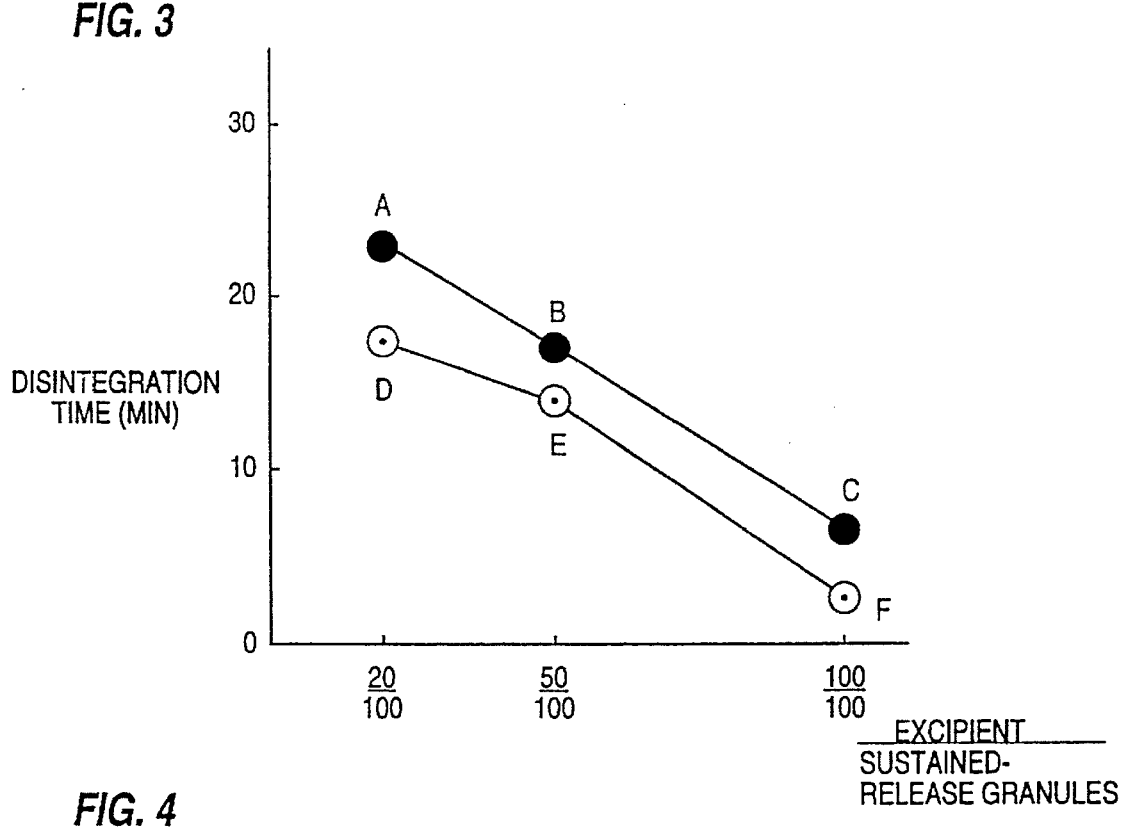
FIG. 3 diagrammatically illustrates results of disintegration tests of Tablets D, E and F in comparison with the results of the disintegration tests of Tablets A, B and C.

Results of the disintegration and coagulation tests are shown in FIG. 3 and Table 4 respectively.

In FIG. 3, plotted points ○ correspond respectively to Tablets D, E and F while plotted points ● correspond respectively to Tablets A, B and C of Example 1, namely, added with no CMC-Ca. Namely, the disintegration time of the sustained-release granules was shortened further by the addition of a disintegrator such as CMC-Ca to the layer-coated granules and moreover, no coagulation of the sustained-release granules was observed after their disintegration.

TABLE 4

(All values are by wt. %)

|  | Tablet | | |
|---|---|---|---|
|  | D | E | F |
| Proportion of coagulated matter | 0 | 0 | 0 |

Example 3

Figure 4:
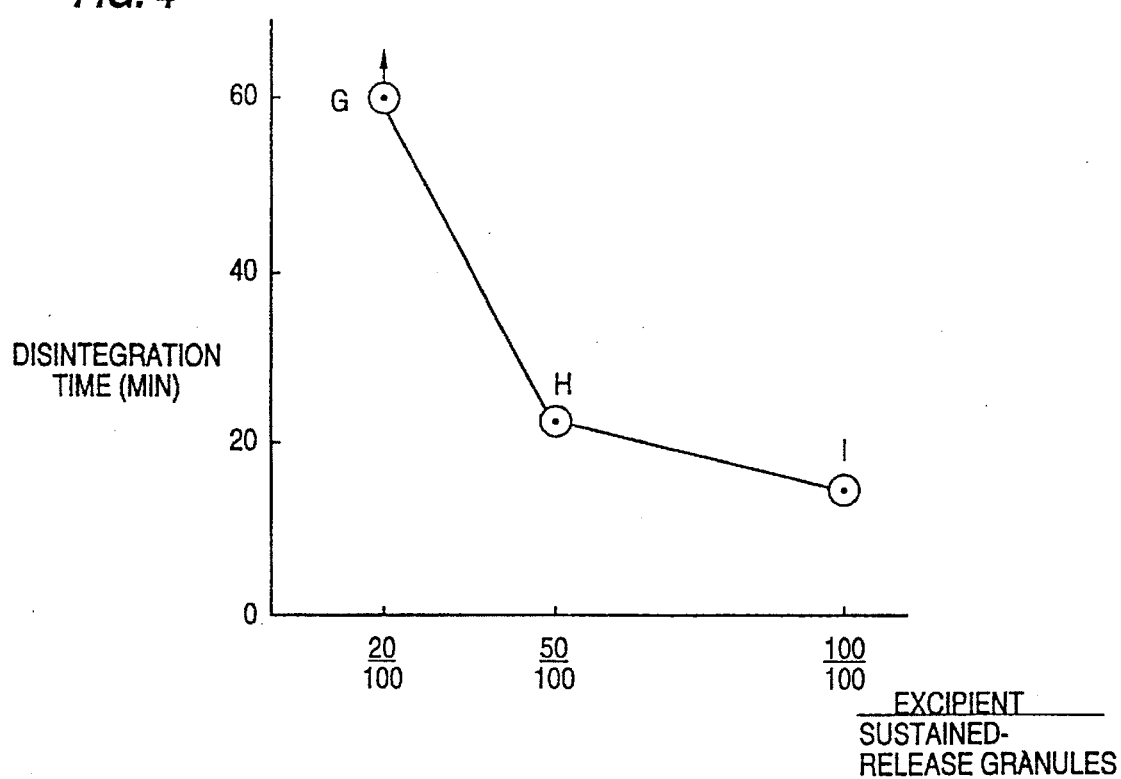
FIG. 4 diagrammatically depicts results of disintegration tests of Tablets G, H and I.

Tablets G, H and I were obtained in accordance with the composition of Example 2 except that corn starch and CMC-Ca were changed respectively to lactose and sodium crosscarmelose. Disintegration and coagulation tests were conducted with respect to those tablets. Results are shown in FIG. 4 and Table 5 Respectively.

TABLE 5

(All values are by wt. %)

|  | Tablet | | |
|---|---|---|---|
|  | G | H | I |
| Proportion of coagulated matter | 0 | 0 | 0 |

Example 4

Sodium crosscarmelose a disintegrator, was separately coated as layers in varied amounts on the surfaces of sustained-release granules. After compression, the state of coagulation of the granules in each tablet was observed.

Namely, sodium crosscarmelose was coated as layers on the surface of the sustained-release granules in the same manner as in Examples 1–3. Then, 200-mg portions of the thus-obtained samples were separately weighed precisely and compression-formed under punching pressures of 200 kg and 400 g/φ=8.0 mm by means of the material testing machine (manufactured by Shimadzu Corp.).

Coagulation and disintegration tests were then conducted separately with respect to the thus-obtained tablets. Compositions and test results are shown in Table 6.

TABLE 6

(All values are parts by weight unless otherwise specifically indicated)

|  |  | Tablet | | | | |
|---|---|---|---|---|---|---|
|  |  | J | K | L | M | N |
| Composition |  |  |  |  |  |  |
| Sustained-release granules |  | 25 | 25 | 25 | 25 | 25 |
| Sodium crosscalmerose |  | 0 | 0.24 | 0.48 | 0.72 | 1.20 |
| PVP K30 |  | 0 | 0.01 | 0.02 | 0.03 | 0.05 |
| Test results |  |  |  |  |  |  |
| Coated layer/sustained-release granules (wt. %) |  | 0 | 1 | 2 | 3 | 5 |
| Compression pressure 200 kg | Proportion of coagulated matter (wt. %) | 100 | 0 | 0 | 0 | 0 |
|  | Disintegration time (min) | >60 | 53 | 34 | 21 | 10 |
| Compression pressure 400 kg | Proportion of coagulated matter (wt. %) | 100 | 12 | 0 | 0 | 0 |
|  | Disintegration time (min) | >60 | >60 | >42 | 25 | 18 |

In Table 6, the sample obtained by compression-forming the sustained-release granules alone (Tablet J) did not disintegrate even 24 hours later. In the case of the samples coated as layers with sodium crosscarmelose on the other hand, no coagulation of the sustained-release granules was observed, for example, at a portion of the coated layers of 1.0 wt. % and up when the compression pressure was 200 kg/φ=8.0 mm.

In the case of Tablet G with about 20% of lactose added based on the sustained-release granules, the tablet did not disintegrate completely and about two thirds remained undisintegrated even after an elapsed time of 60 minutes later in the disintegration test. However, no coagulation among the sustained-release granules was observed in the coagulation test. It is hence appreciated that when lactose is added in a small amount, the disintegration time becomes longer but no coagulation occurs among the sustained-release granules and the tablet undergoes disintegration similar to that of a multiple unit.

Example 5

Using a 20-l Henschel mixer, portions of sustained-release granules were separately layer-coated to give mixing proportions (weight proportions) shown in Table 6. The formulation procedure of Examples 1–3 was followed. Each portion of the sustained-release granules was charged in the mixer. Thereafter, the excipients, disintegrator and binder were coated as layers on the sustained-release granules while adding their ethanol solution little by little to the sustained-release granules. Results of disintegration and coagulation tests are also shown in Table 7.

TABLE 7

(All figures are parts by weight unless otherwise specifically indicated)

|  | Tablet | |
| --- | --- | --- |
|  | P | Q |
| Sustained-release granules | 1000 | 1000 |
| Avicel for drug and food application | 475 | — |
| Mannitol | — | 950 |
| CMC-Ca | 25 | 50 |
| PVP K30 | 10 | 20 |
| Disintegration time (minutes) | 36.0 | 19.5 |
| Proportion of coagulated matter (wt. %) | 0 | 0 |

Example 6

Tablets, which were able to show dispersion similar to that of multiple units, were formulated by using sustained-release granules containing bunazosin hydrochloride as an active substance. The sustained-release granules are cylindrical granules prepared by using a screen whose openings had a diameter of 0.5 mm. When the sustained-release granules were compression-formed as they were, they did not integrate and did not show dispersion similar to that of multiple units.

Using a fluidized centrifugal granulator CF 360 (trade name; manufactured by Freund Sangyo K.K.), formulation adjuvants suspended in 2400 ml of ethanol were added little by little so that they were caused to deposit as layers on the sustained-release granules containing bunazosin hydrochloride and the following composition was achieved.

| Composition (parts by weight) | |
| --- | --- |
| Sustained-release granules (content of bunazosin hydrochloride: 10%) | 750 |
| Lactose | 705 |
| CMC-Ca | 30 |
| HPC-L | 15 |

The thus-obtained layer-coated granules were added with calcium stearate in an amount of 0.2 wt. %. Under punching conditions consisting of a revolution speed of 30 rpm and a compression pressure of 0.6–0.7 ton/punch, the resultant mixture was then formed into tablets at a rate of 75 mg per tablet by punches having a diameter of 5.5 mm.

Results of disintegration and coagulation tests are as follows.

| Test results | |
| --- | --- |
| Disintegration time (6 tablets) | 2.6–9.3 minutes |
| Proportion of coagulated matter | 0 wt. % |

In addition, a dissolution test was also conducted by the paddle method. Results are given below. The test was carried out under the following conditions. Namely, the tablets were dissolved for 2 hours with the first solution of the Japan Pharmacopoeia and after adjustment of the pH, the dissolution was continued with the second solution of the Japan Pharmacopoeia.

| Results of the dissolution test: | | | | | |
| --- | --- | --- | --- | --- | --- |
|  | Time (hours) | | | | |
|  | 1 | 2 | 4 | 6 | 8 |
| wt. % | 7.9 | 21.4 | 46.1 | 67.5 | 83.2 |

Example 7

In order to use coated layers as fast-acting portions of an active substance, bunazosin hydrochloride was added as an active substance in the coated layers. Tablets were prepared by the same formulation procedure and under the same formulation conditions as those employed in Example 5. Composition and respective test results are as follows:

| Composition (parts by weight) | |
| --- | --- |
| Sustained-release granules (content of bunazosin hydrochloride: 8%) | 750 |
| Bunazosin hydrochloride | 15 |
| Lactose | 690 |
| CMC-Ca | 30 |
| HPC-L | 15 |

| Results of disintegration and coagulation tests | |
| --- | --- |
| Disintegration time (6 tablets) | 9.4–11.8 minutes |
| Proportion of coagulated matter | 0 wt. % |

| Results of the dissolution test: | | | | |
| --- | --- | --- | --- | --- |
|  | Time (hours) | | | |
|  | 2 | 4 | 6 | 8 |
| wt. % | 44.1 | 63.4 | 79.3 | 90.5 |

Having now fully described the invention, it will be apparent to one of ordinary skill in the art that many changes and modifications can be made thereto without departing from the spirit or scope of the invention as set forth herein.

We claim:

1. A process for the production of a sustained-release pharmaceutical tablet, which comprises the steps of:

mixing a drug with a sustained-release substance to prepare a plurality of sustained-release granules, wherein the active substance is bunazosin hydrochloride and wherein the sustained-release substance is at least one member selected from the group consisting of sucrose-fatty acid ester, ethyl cellulose, methyl cellulose, polyvinyl pyrrolidone, hydroxypropyl cellulose, hydroxypropylmethyl cellulose, a gum arabic, gelatin and shellac;

laminating each of the resulting granules with a water-dispersible excipient to prepare laminated sustained-release granules; and mixing the resulting laminated granules with a lubricant; and compressing the laminated granules and lubricant to obtain the sustained-release pharmaceutical tablet.

2. A process according to claim 1, wherein the water-dispersible excipient is at least one member selected from the group consisting of crystalline cellulose, corn starch, silicic acid, magnesium silicate and aluminum silicate.

3. A process according to claim 1, wherein the first or second formulation adjuvant or both contain at least one member selected from the group consisting of binders and disintegrators.

4. A process according to claim 3, wherein the binder is selected from the group consisting of hydroxypropylcellulose, polyvinyl pyrrolidone, polyethylene glycol, and methyl cellulose.

5. A process according to claim 3, wherein the disintegrator is selected from the group consisting of carboxy methyl cellulose, calcium salt of carboxy methyl cellulose, and sodium crosscarmelose.

6. An improved oral pharmaceutical sustained-release multi-granule tablet, produced by a process which consists essentially of the steps of:

preparing, as nuclear granules, a plurality of sustained-release granules containing an active substance and a sustained-release substance, wherein the active substance is bunazosin hydrochloride and wherein the sustained-release substance is at least one member selected from the group consisting of sucrose-fatty acid ester, ethyl cellulose, methyl cellulose, polyvinyl pyrrolidone, hydroxypropyl cellulose, hydroxypropylmethyl cellulose, a gum arabic, gelatin and shellac;

coating, in a laminate style, each of said sustained-release granules with at least one layer composed of a first formulation adjuvant or a mixture of the first formulation adjuvant and the active substance, wherein the first formulation adjuvant comprises a water-dispersible excipient; and compressing said coated sustained-release granules with a second formulation adjuvant comprising a lubricant to obtain the sustained-release multi-granule tablet.

7. A tablet according to claim 6, wherein the water-dispersible excipient is at least one member selected from the group consisting of crystalline cellulose, corn starch, silicic acid, magnesium silicate and aluminum silicate.

8. A tablet according to claim 6, wherein the first or second formulation adjuvant or both contain at least one member selected from the group consisting of binders and disintegrators.

9. A tablet according to claim 8, wherein the binder is selected from the group consisting of hydroxypropylcellulose, polyvinyl pyrrolidone, polyethylene glycol, and methyl cellulose.

10. A tablet according to claim 8, wherein the disintegrator is selected from the group consisting of carboxy methyl cellulose, calcium salt of carboxy methyl cellulose, and sodium crosscarmelose.

11. A tablet according to claim 6, wherein each of said sustained-release granules are coated with a plurality of layers of the first formulation adjuvant or the mixture of the first formulation adjuvant and the active substance.

12. A process according to claim 1, wherein each of said sustained-release granules are coated with a plurality of layers of the first formulation adjuvant or the mixture of the first formulation adjuvant and the active substance.

13. An improved oral pharmaceutical sustained-release multi-granule tablet, comprising:

a plurality of sustained-release granules comprising an active substance and a sustained-release substance, wherein the active substance is bunazosin hydrochloride and wherein the sustained-release substance is at least one member selected from the group consisting of sucrose-fatty acid ester, ethyl cellulose, methyl cellulose, polyvinyl pyrrolidone, hydroxypropyl cellulose, hydroxypropylmethyl cellulose, a gum arabic, gelatin and shellac, each of said sustained-release granules having an outer coating comprising at least one layer composed of a first formulation adjuvant or a mixture of the first formulation adjuvant and the active substance, wherein the first formulation adjuvant is a water-dispersible excipient;

the plurality of granules and a second formulation adjuvant comprising a lubricant being compressed in a tablet form.

14. A tablet according to claim 13, wherein the water-dispersible excipient is at least one member selected from the group consisting of crystalline cellulose, corn starch, silicic acid, magnesium silicate and aluminum silicate.

15. A tablet according to claim 13, wherein the first or second formulation adjuvant or both contain at least one member selected from the group consisting of binders and disintegrators.

16. A tablet according to claim 15, wherein the binder is selected from the group consisting of hydroxypropylcellulose, polyvinyl pyrrolidone, polyethylene glycol, and methyl cellulose.

17. A tablet according to claim 15, wherein the disintegrator is selected from the group consisting of carboxy methyl cellulose, calcium salt of carboxy methyl cellulose, and sodium crosscarmelose.

18. A tablet according to claim 13, wherein each of said sustained-release granules are coated with a plurality of layers of the first formulation adjuvant or the mixture of the first formulation adjuvant and the active substance.

19. A process for producing an improved oral pharmaceutical sustained-release multi-granule tablet, which consists essentially of the steps of:

preparing, as nuclear granules, a plurality of sustained-release granules containing an active substance and a sustained-release substance, wherein the active substance is bunazosin hydrochloride and wherein the sustained-release substance is at least one member selected from the group consisting of sucrose-fatty acid ester, ethyl cellulose, methyl cellulose, polyvinyl pyrrolidone, hydroxypropyl cellulose, hydroxypropylmethyl cellulose, a gum arabic, gelatin and shellac;

coating, in a laminate style, each of said sustained-release granules with at least one layer composed of a first formulation adjuvant or a mixture of the first formulation adjuvant and the active substance, wherein the first formulation adjuvant comprises a water-dispersible excipient; and compressing said coated sustained-release granules with a second formulation adjuvant comprising a lubricant to obtain the sustained-release multi-granule tablet.

20. A process according to claim 19, wherein each of said sustained-release granules are coated with a plurality of layers of the first formulation adjuvant or the mixture of the first formulation adjuvant and the active substance.

21. A process according to claim 19, wherein the water-dispersible excipient is at least one member selected from the group consisting of crystalline cellulose, corn starch, silicic acid, magnesium silicate and aluminum silicate.

22. A process according to claim 19, wherein the first or second formulation adjuvant or both contain at least one member selected from the group consisting of binders and disintegrators.

23. A process according to claim 22, wherein the binder is selected from the group consisting of hydroxypropylcellulose, polyvinyl pyrrolidone, polyethylene glycol, and methyl cellulose.

24. A process according to claim 22, wherein the disintegrator is selected from the group consisting of carboxy methyl cellulose, calcium salt of carboxy methyl cellulose, and sodium crosscarmelose.

* * * * *